US012402870B2

(12) United States Patent
Zhao et al.

(10) Patent No.: US 12,402,870 B2
(45) Date of Patent: Sep. 2, 2025

(54) BIOADHESIVE MATERIALS AND MINIMALLY INVASIVE METHODS FOR ADHERING TISSUES WITH BIOADHESIVE MATERIALS

(71) Applicants: Massachusetts Institute of Technology, Cambridge, MA (US); Mayo Foundation for Medical Education and Research, Rochester, MN (US)

(72) Inventors: Xuanhe Zhao, Allston, MA (US); Hyunwoo Yuk, Cambridge, MA (US); Sarah J Wu, Cambridge, MA (US); Christoph Nabzdyk, Rochester, MN (US)

(73) Assignees: MASSACHUSETTS INSTITUTE OF TECHNOLOGY, Cambridge, MA (US); MAYO FOUNDATION FOR MEDICAL EDUCATION AND RESEARCH, Rochester, MN (US)

(*) Notice: Subject to any disclaimer, the term of this patent is extended or adjusted under 35 U.S.C. 154(b) by 501 days.

(21) Appl. No.: 17/497,497

(22) Filed: Oct. 8, 2021

(65) Prior Publication Data
US 2022/0110619 A1    Apr. 14, 2022

Related U.S. Application Data

(60) Provisional application No. 63/091,105, filed on Oct. 13, 2020.

(51) Int. Cl.
| | |
|---|---|
| *A61B 17/00* | (2006.01) |
| *A61B 17/072* | (2006.01) |
| *A61L 24/06* | (2006.01) |
| *A61M 25/10* | (2013.01) |

(52) U.S. Cl.
CPC .. *A61B 17/00491* (2013.01); *A61B 17/07292* (2013.01); *A61L 24/06* (2013.01);
(Continued)

(58) Field of Classification Search
CPC ............ A61M 25/10; A61B 17/00234; A61B 17/00491; A61B 17/0057;
(Continued)

(56) References Cited

U.S. PATENT DOCUMENTS

| | | | | |
|---|---|---|---|---|
| 2010/0274280 | A1* | 10/2010 | Sawhney | ............ A61L 24/0031 606/213 |
| 2016/0367235 | A1* | 12/2016 | Campbell | .......... A61B 17/0057 |
| 2020/0038005 | A1* | 2/2020 | Smith | ............... A61B 17/00234 |

FOREIGN PATENT DOCUMENTS

| | | |
|---|---|---|
| EP | 3153194 | 10/2019 |
| JP | 2011502582 A | 1/2011 |

(Continued)

OTHER PUBLICATIONS

International Search Report for PCT/US21/54170 mailed Jan. 24, 2022.
(Continued)

*Primary Examiner* — Mohamed G Gabr
(74) *Attorney, Agent, or Firm* — Nieves IP Law Group, LLC; Peter A. Nieves

(57) ABSTRACT

Bioadhesive materials and methods for adhering biological tissues and blood vessels in a minimally invasive manner, wherein the bioadhesive materials are in folded bioadhesive sleeve configurations or in injectable bioadhesive forms adapted for delivery using minimally invasive procedures. The folded bioadhesive sleeve is disposed on the distal portions of a variety of minimally invasive devices for insertion to a target tissue site, then deployed and adhered to the target tissue site through actuation of the minimally
(Continued)

invasive device. The injectable bioadhesive is disposed in a syringe and delivered to a target site via a catheter, then adhered to the target tissue by actuation of a minimally invasive device. Precise placement and adhesion to the target tissue site can be successfully accomplished solely through the actuation of the minimally invasive devices without the use of additional devices to assist in placement or actuation of the bioadhesive materials.

14 Claims, 8 Drawing Sheets

(52) U.S. Cl.
CPC ............... *A61B 2017/00526* (2013.01); *A61B 2017/00938* (2013.01); *A61L 2400/06* (2013.01); *A61M 25/10* (2013.01)

(58) Field of Classification Search
CPC .... A61B 17/07292; A61B 2017/00526; A61B 2017/00557; A61B 2017/0065; A61B 2017/00659; A61B 2017/00938; A61B 2017/00951; A61L 24/001; A61L 24/0094; A61L 24/06; A61L 2400/06
See application file for complete search history.

(56) References Cited

FOREIGN PATENT DOCUMENTS

| | | |
|---|---|---|
| WO | 2009059217 | 5/2009 |
| WO | 2020028297 | 2/2020 |

OTHER PUBLICATIONS

Annabi, "Elastic sealants for surgical applications", European Journal of Pharmaceutics and Biopharmaceutics 95 (2015) 27-39.
Taboada, "Overcoming the translational barriers of tissue adhesives", Nature Reviews | Materials, 2020.
Bass, L. S., & Treat, M. R. Laser tissue welding: A comprehensive review of current and future. Lasers in Surgery and Medicine, 17(4), 315-349 (1995).
Mueller M.R. et al., The anticipation and management of air leaks and residual spaces post lung resection. J Thorac Dis. 6(3), 271-284(2014).
N. D'souza et al., Migrated esophageal stent posing a challenge for ventilation. Saudi Journal of Anaesthesia 11, 215 (2017).
J. Amour et al., Emergency treatment of tracheobronchial stent migration. Anesthesiology: The Journal of the American Society of Anesthesiologists 101, 1230-1232 (2004).
O. Karatepe et al., Esophageal stent migration can lead to intestinal obstruction. North American Journal of Medical Sciences 1, 63 (2009).
Knapps J. et al., A systematic review of staple-line reinforcement in laparoscopic sleeve gastrectomy. JSLS, 17(3), 390-399(2013).
Wang, Z. et al., The Efficacy of Staple Line Reinforcement during Laparoscopic Sleeve Gastrectomy: A Meta-Analysis of Randomized Controlled Trials. International Journal of Surgery 25, 145-52(2016).

\* cited by examiner

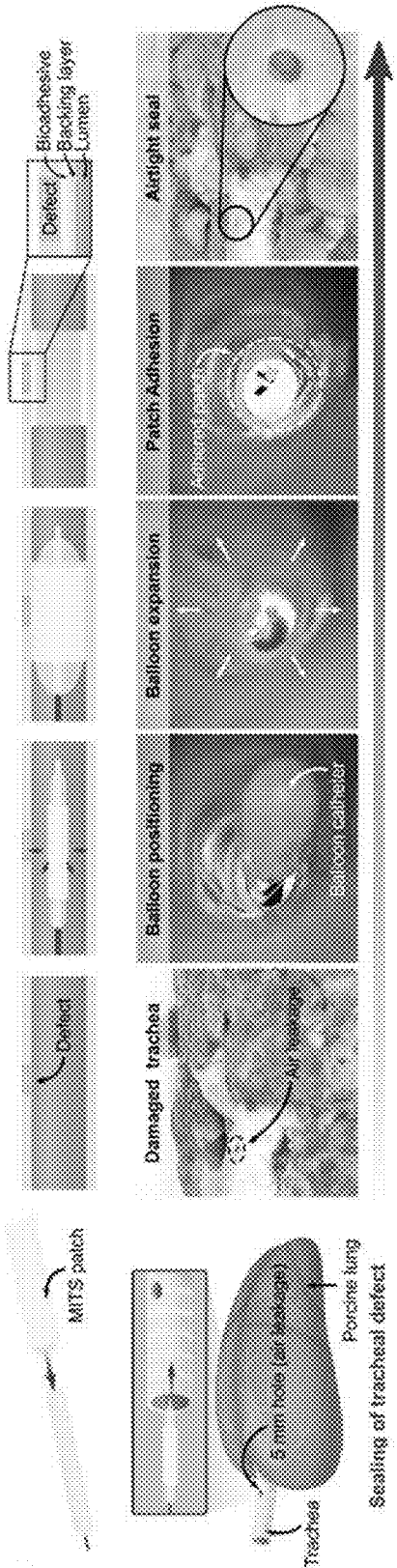
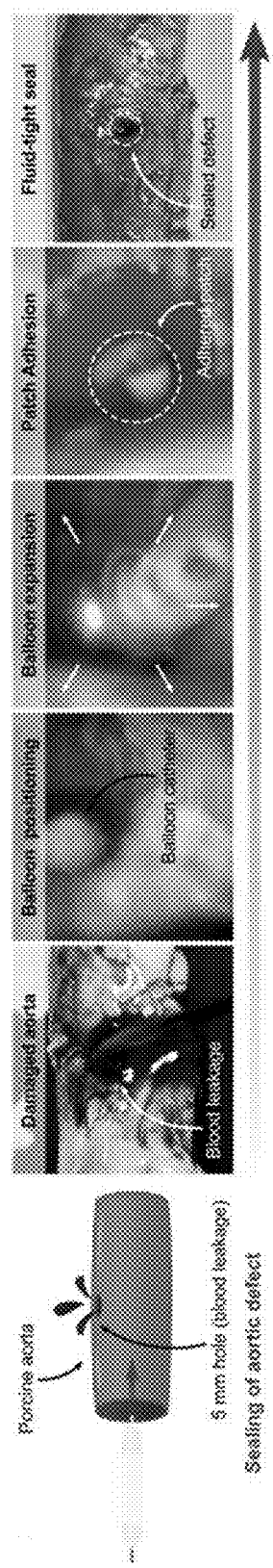
FIG. 4A
FIG. 4B
FIG. 4C
FIG. 4D

BIOADHESIVE MATERIALS AND MINIMALLY INVASIVE METHODS FOR ADHERING TISSUES WITH BIOADHESIVE MATERIALS

CROSS-REFERENCE TO RELATED APPLICATIONS

This application claims the benefit of priority to U.S. Provisional Patent Application No. 63/091,105, entitled BIOADHESIVE MATERIALS AND MINIMALLY INVASIVE METHODS FOR ADHERING TISSUES WITH BIOADHESIVE MATERIALS, which was filed on Oct. 13, 2020. The disclosure of the prior application is incorporated by reference herein in its entirety.

GOVERNMENT SUPPORT STATEMENT

This invention was made with Government support under Grant No. EFMA-1935291 awarded by the National Science Foundation. The Government has certain rights in the invention.

FIELD OF THE INVENTION

The present invention generally relates to bioadhesive materials and methods for adhering biological tissues and blood vessels in a minimally invasive manner. More particularly, the present invention relates to methods for delivering and adhering bioadhesive materials using a minimally invasive surgical or diagnostic instrument, wherein the bioadhesive material is configured for integration with and direct deployment by the minimally invasive surgical or diagnostic instrument.

BACKGROUND OF THE INVENTION

Methods for sealing or joining tissues in minimally invasive surgery typically utilize sutures, staples, clips, or laser welding, each of which exhibit a variety of limitations. Each of these methods can cause mechanical or thermal tissue damage, and suturing and laser welding are considerably tedious maneuvers requiring surgeons to suture or weld individual points along a line (N. Annabi et al., Elastic sealants for surgical applications. *European Journal of Pharmaceutics and Biopharmaceutics* 95, 27-39 (2015); G. M. Taboada et al., Overcoming the translational barriers of tissue adhesives. *Nature Reviews Materials,* 1-20 (2020); Bass, L. S., & Treat, M. R. Laser tissue welding: A comprehensive review of current and future. *Lasers in Surgery and Medicine,* 17(4), 315-349 (1995)). Staplers carry the risk of misfiring and/or malformation, which can result in leaky staple lines and other adverse effects for the patient. Furthermore, under certain medical circumstances, tissues might be too fragile to hold sutures and/or staples in place, which can result in tissue breakdown and separation of the suture or staple line. For example, parenchymal tears caused by the ripping of fragile lung tissue through these pointwise tissue sealing modalities can substantially impact morbidity and prolonged hospitalizations (Mueller M. R. et al., The anticipation and management of air leaks and residual spaces post lung resection. *J Thorac Dis.* 6(3), 271-284 (2014)).

In addition to sutures and staples, stent-grafts have been deployed in luminal structures such as the trachea, the esophagus, and segments of the gastrointestinal tract to cover wall perforations. However, their clinical efficacy is limited by insufficient sealing performance and a high tendency to migrate away from their deployment position, which can lead to medical and surgical emergencies. (N. D'souza et al., Migrated esophageal stent posing a challenge for ventilation. *Saudi Journal of Anaesthesia* 11, 215 (2017); J. Amour et al., Emergency treatment of tracheobronchial stent migration. *Anesthesiology: The Journal of the American Society of Anesthesiologists* 101, 1230-1232 (2004); O. Karatepe et al., Esophageal stent migration can lead to intestinal obstruction. *North American Journal of Medical Sciences* 1, 63 (2009)). This is a particularly common adverse outcome for stent-grafts that are deployed in the airway and gastrointestinal tract and frequently leads to failure of the tenuous seal, requiring additional procedures with stent-graft repositioning or stent-graft retrieval.

An endoscopic articulating stapler that is maneuverable through small ports has been designed to cut and seal segments of tissue by clamping the desired tissue site between an anvil and a stapler cartridge, firing parallel lines of staples, and then actuating a blade to cut the tissue in between the two staples lines. However, as discussed, surgical staplers have substantial device failure rates, and the mode of tissue sealing is associated with tissue damage and subsequent risk of suture line failure.

Currently, there are several products which attempt to mitigate the leakage and separation of surgical staples by applying a reinforcing material or spray in order to buttress staple lines, including PERI-STRIPS®, GORE SEAMGUARD®, Evicel™, and Tisseel™. In systematic reviews of clinical results, while such staple line reinforcements have been found to diminish bleeding after laparoscopic sleeve gastrectomies, they did not lower the postoperative leak rates (Knapps J. et al., A systematic review of staple-line reinforcement in laparoscopic sleeve gastrectomy. *JSLS,* 17(3), 390-399(2013); Wang, Z. et al., The Efficacy of Staple Line Reinforcement during Laparoscopic Sleeve Gastrectomy: A Meta-Analysis of Randomized Controlled Trials. *International Journal of Surgery* 25, 145-52(2016)).

Thus, there exists a need for improved methods, adhesives, and devices that achieve fast, robust tissue sealing that can be performed minimally invasively, either as reinforcements to or replacements of surgical suture/staple lines.

SUMMARY OF THE INVENTION

According to one aspect, the present invention provides a folded bioadhesive sleeve for introduction to a target tissue surface using minimally invasive techniques comprising a multilayer bioadhesive material comprising a dry bioadhesive layer having a bottom surface and a top surface, and a non-adhesive layer disposed on the top surface of the dry bioadhesive layer. The multilayer bioadhesive material is in the configuration of a multilayer bioadhesive patch, tape, film, strip, or sheet, wherein the multilayer bioadhesive materials is folded into a hollow sleeve shape comprising an inner passageway and an outer surface, wherein the inner passageway is defined by an inner surface formed of portions of the non-adhesive layer, and wherein the outer surface is an adhesive surface.

According to another aspect, the present invention provides a folded bioadhesive sleeve for introduction to a target tissue surface using minimally invasive techniques comprising a non-adhesive sleeve layer is adapted for fitting on an exterior distal end portion of a minimally invasive device, and one or more adhesive portions comprising at least a dry bioadhesive layer having a bottom surface and a top surface disposed on the non-adhesive sleeve layer. The one or more adhesive portions are positioned for contacting the target tissue surface and receiving pressure against the target tissue surface upon actuation of the minimally invasive device.

Embodiments according to these aspects can include one or more of the following features. The dry bioadhesive layer has a liquid content such that placement of a surface of the dry bioadhesive layer in contact with the target tissue surface causes the dry bioadhesive layer to absorb liquid present on the target tissue surface, swell to form temporary crosslinking between the dry bioadhesive layer and the target tissue surface, and form covalent crosslinking between the dry bioadhesive layer and the target tissue surface. The folded bioadhesive further comprises a hydrophobic overlayer disposed on the bottom surface of the dry bioadhesive layer. The hydrophobic overlayer comprises one or more hydrophobic fluids. The folded bioadhesive further comprises a backing layer disposed on the top surface of the dry bioadhesive layer, where the backing layer is disposed between the dry bioadhesive layer and the non-adhesive sleeve layer. The non-adhesive layer and/or backing layer comprises a biocompatible polymer or polymer blend. The biocompatible polymer or polymer blend is selected from polyacrylic acid, polyacrylamide, polyvinyl alcohol, polyhydroxy ethyl methacrylate, polyethylene glycol, polyvinylpyrrolidone, polyurethane, polydimethylsiloxane, polyvinyl chloride, styrene-ethylene-butylene-styrene (SEBS), gelatin, chitosan, alginate, polycaprolactone, polylactic acid, poly(lactic-co-glycolic acid), and combinations thereof, functionalized with an interpenetrated network of one or more zwitterionic polymers. The dry bioadhesive layer comprises (i) one or more hydrophilic polymers or copolymers; (ii) one or more amine coupling groups, and (iii) one or more cross linkers. The bottom surface of the dry bioadhesive layer is micro-textured. The micro-textured surface comprises a plurality of surface imbedded microparticles, 3D printed micropatterns, embossed micropatterns, molded micro-textures, patterned micro-textures, surface etched textures, spun micro- or nano-fibers, or combinations thereof. The folded configuration is an origami-based design of a triangular sleeve having a triangular shaped inner passageway. The triangular sleeve is sized and shaped for housing a distal portion of a minimally invasive device. The minimally invasive device is a balloon catheter, and the triangular sleeve is sized and shaped for housing an uninflated balloon. The folded configuration is an origami-based design of a pleated cylindrical sleeve with a plurality of wings. The pleated cylindrical sleeve is sized and shaped for housing a distal portion of a minimally invasive device. The minimally invasive device is a balloon catheter, and the pleated cylindrical sleeve is sized and shaped for housing an uninflated balloon. The folded bioadhesive sleeve further comprises one or more stabilizing elements disposed on the bioadhesive, the one or more stabilizing elements configured for attachment to a minimally invasive device.

According to another aspect, the present invention provides a bioadhesive material for introduction to a target tissue surface using minimally invasive techniques, wherein the bioadhesive material comprises a hydrophobic matrix and plurality of bioadhesive microparticles dispersed within the hydrophobic matrix so as to form an injectable bioadhesive material.

Embodiments according to these aspects may include one or more of the following features The injectable bioadhesive material is disposable within a syringe for delivery through a catheter using minimally invasive techniques. The dry bioadhesive microparticles comprises (i) one or more hydrophilic polymers or copolymers; (ii) one or more amine coupling groups, and (iii) one or more cross linkers. The hydrophobic matrix is in the form of a protective matrix around the dispersed bioadhesive microparticles that protects the bioadhesive microparticles from fluid in the environment. The adhesive material is structured such that disposing the adhesive material directly on a surface and applying pressure to the adhesive material causes (a) the hydrophobic matrix to repel fluid on the surface, (b) the bioadhesive particles to compress forming an adhesive layer, and (c) the bioadhesive particles to form temporary crosslinks followed by covalent crosslinks with the surface. The one or more hydrophilic polymers or copolymers are selected from hydrophilic polymers or copolymers that absorb water at a dry state. The hydrophobic matrix is selected from silicone oils, mineral oils, essential oils, perfluoropolyether oils, lanolin oils, and combinations thereof. The adhesive material is biocompatible. The bioadhesive microparticles have a particle size ranging from about 10 µm to about 200 µm. A ratio between the bioadhesive microparticles and the hydrophobic matrix ranges from about 1:3 to about 1:0.5.

According to another aspect, the present invention provides a method of forming a folded bioadhesive sleeve for introduction to a target tissue surface using minimally invasive techniques comprising: forming a dry bioadhesive layer having a bottom surface and a top surface; disposing and attaching a non-adhesive layer on the top surface of the dry bioadhesive layer to form a multilayer adhesive in the form of a patch, tape, film, strip, or sheet; folding the multilayer adhesive into a folded origami-based configuration comprising a hollow sleeve having an inner passageway and an outer surface, wherein the inner passageway is defined by an inner surface formed of portions of the non-adhesive layer, and wherein the outer surface is an adhesive surface.

Embodiments according to these aspects can include one or more of the following features. The hollow sleeve is in the form of an triangular sleeve having a triangular shaped inner passageway. The triangular sleeve is folded into a size and shape for housing a distal portion of a minimally invasive device. The minimally invasive device is a balloon catheter, and the triangular sleeve folded into a size and shape for housing an uninflated balloon. The hollow sleeve comprises a pleated cylindrical sleeve with a plurality of wings. The pleated cylindrical sleeve is folded into a size and shape for housing a distal portion of a minimally invasive device. The minimally invasive device is a balloon catheter, and the pleated cylindrical sleeve is folded into a size and shape for housing an uninflated balloon.

According to another aspect, the present invention provides a method of forming a folded bioadhesive sleeve for introduction to a target tissue surface using minimally invasive techniques comprising: forming a non-adhesive layer in a shape configured to fold and fit on a distal portion of a minimally invasive device; disposing one or more adhesive portions on the non-adhesive layer, the one or more adhesive portions being positioned for contacting the target tissue surface and receiving pressure against the target tissue surface upon actuation of the minimally invasive device, the one or more adhesive portions comprising at least a dry bioadhesive layer having a bottom surface and a top surface disposed on the non-adhesive sleeve layer; and folding the non-adhesive layer into the folded bioadhesive sleeve configuration.

Embodiments according to these aspects can include one or more of the following features. The minimally invasive device is an endoscopic articulating linear stapler having two opposing jaws, wherein the sleeve is configured to fit over the two opposing jaws of the stapler with the one or more adhesive portions positioned on inner surfaces of the two opposing jaws. Adhesive portions are rectangular multilayer adhesive portions.

According to another aspect, the present invention provides a method of adhering a bioadhesive to a tissue surface using a minimally invasive techniques, wherein the tissue surface is an inner surface of a hollow organ or vessel, comprising: (a) providing a folded bioadhesive sleeve comprising a multilayer bioadhesive material comprising a dry bioadhesive layer having a bottom surface and a top surface, and a non-adhesive layer disposed on the top surface of the dry bioadhesive layer, wherein the multilayer bioadhesive material is in the configuration of a multilayer bioadhesive patch, tape, film, strip, or sheet, wherein the multilayer bioadhesive materials is folded into a hollow sleeve shape comprising an inner passageway and an outer surface, wherein the inner passageway is defined by an inner surface formed of portions of the non-adhesive layer, and wherein the outer surface is an adhesive surface; (b) providing a balloon catheter device having an uninflated balloon on a distal end thereof; (c) disposing the folded bioadhesive sleeve over the uninflated balloon, with the inner passageway at least partially housing the uninflated balloon, and wherein the inner surface of the folded bioadhesive sleeve is in contact with the uninflated balloon; (d) inserting the balloon catheter device into the hollow organ or vessel at a target tissue surface site using the minimally invasive techniques; (e) inflating the balloon and allowing the folded bioadhesive sleeve to unfurl such that the outer adhesive surface contacts the inner surface of the hollow organ or vessel; and (f) allowing a combination of hydration of the dry bioadhesive layer in the presence of body fluids and radial pressure exerted by the inflated balloon to release the folded configuration, conform the bioadhesive material to the inner surface of the hollow organ or vessel, and trigger adhesion of the bioadhesive material to the inner surface of the hollow organ or vessel.

According to another aspect, the present invention provides a method of adhering an adhesive layer to a target tissue surface using a minimally invasive techniques comprising: (a) providing a folded bioadhesive sleeve for introduction to a target tissue surface using minimally invasive techniques comprising a non-adhesive sleeve layer is adapted for fitting on an exterior distal end portion of a minimally invasive device, and one or more adhesive portions comprising at least a dry bioadhesive layer having a bottom surface and a top surface disposed on the non-adhesive sleeve layer, wherein the one or more adhesive portions are positioned for contacting the target tissue surface and receiving pressure against the target tissue surface upon actuation of the minimally invasive device; (b) providing an articulating linear stapler having two opposing jaws; (c) disposing the folded bioadhesive sleeve over the two opposing jaws with the one or more adhesive portions disposed on inner surfaces of the two opposing jaws, wherein the two opposing jaws are in an open position with a space therebetween; (d) inserting the articulating linear stapler to a target tissue surface site using the minimally invasive techniques, wherein the target tissue surface is disposed between the two opposing jaws; (e) actuating the articulating linear stapler by closing the two opposing jaws on the target tissue surface, wherein the one or more adhesive portions contact and the target tissue surface; and (f) allowing a combination of hydration of the dry bioadhesive layer in the presence of body fluids and pressure exerted by the two opposing jaws to trigger adhesion of the one or more adhesive portions to the target tissue surface.

According to another aspect, the present invention provides method of adhering one or more tissue surfaces covered in one or more fluids comprising: (a) applying an adhesive material directly to one or more of the fluid covered tissue surfaces, the adhesive material comprising: a hydrophobic matrix; and a plurality of bioadhesive microparticles dispersed within the hydrophobic matrix, the bioadhesive microparticles comprising: (i) one or more hydrophilic polymers or copolymers; (ii) one or more amine coupling groups, and (iii) one or more cross linkers; (b) applying pressure ranging from about 1 kPa to 50 kPa to the adhesive material; (c) allowing the hydrophobic matrix to repel and clean the one or more fluids from the tissue surfaces; (d) allowing physical bond forming group in the bioadhesive microparticles to form temporary crosslinks by intermolecular bonds; and (e) allowing amine coupling groups in the bioadhesive microparticles to form covalent crosslinks with the tissue surfaces.

Embodiments according to these aspects may include one or more of the following features. Pressure is applied for about 5 seconds to about 30 seconds. The adhesive material is an injectable adhesive material, and the adhesive material is applied using a syringe. The bioadhesive microparticles have a particle size ranging from about 10 μm to about 200 μm. The adhesive material comprises a ratio between the bioadhesive microparticles and the hydrophobic matrix ranging from about 1:3 to about 1:0.5. After (a) applying an adhesive material directly to one or more of the fluid covered tissue surfaces and prior to (b) applying pressure, the method further comprises applying a backing material to the adhesive material and wherein (b) applying pressure comprises applying pressure to the adhesive material via the backing material. The backing material is fabricated of a biocompatible material that does not adhere to wet surfaces. The backing material is fabricated of oxidized cellulose, silicone elastomer, polyurethane, hydrogel, any other biocompatible materials that do not adhere to wet tissue, and combinations thereof.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIGS. 1A-B illustrate photographs of an origami-based design of a bioadhesive material for integration with minimally invasive instruments according to an embodiment of the present invention, wherein an exemplary bioadhesive material in the plastically-deformable dry glassy state is depicted prior to and after folding into a target origami structure and which, upon hydration, transitions to a rubbery state and becomes a soft conformable hydrogel, and FIG. 1C illustrates a catheter-based delivery of an injective bioadhesive to the target tissue, where in the injectable bioadhesive comprises dry bioadhesive microparticles dispersed within a hydrophobic fluid.

FIGS. 4A-D schematically illustrate ex vivo demonstrations of minimally invasive delivery and application of a bioadhesive material by balloon catheters according to embodiments of the preset invention, with FIG. 4A generally illustrating bioadhesive material integration and delivery using a balloon catheter, FIG. 4B showing macroscopic and endoscopic photographs of the air-tight sealing of a porcine tracheal defect (5-mm hole) by a folded bioadhesive patch according to an embodiment of the preset invention as delivered and applied via a Foley catheter, FIG. 4C showing macroscopic and endoscopic photographs of the fluid-tight sealing of a porcine esophageal defect (5-mm hole) by a folded bioadhesive patch according to an embodiment of the preset invention as delivered and applied via an esophageal catheter, FIG. 4D showing macroscopic and endoscopic photographs of the fluid-tight sealing of a porcine aortic defect (5-mm hole) by a folded bioadhesive patch according to an embodiment of the preset invention as delivered and applied via a Foley catheter.

FIGS. 7A-C schematically illustrates ex vivo demonstrations of minimally invasive delivery and application of a folded bioadhesive material by surgical staplers according to an embodiment of the preset invention, wherein FIG. 7A shows bioadhesive patch integration and delivery using a linear stapler, FIG. 7B shows macroscopic photographs of the fluid-tight sealing of a porcine intestinal defect (5-mm hole) by the bioadhesive patch delivered and applied via the articulating linear stapler, and FIG. 7C shows endoscopic photographs of a porcine intestinal defect (5-mm hole) sealing by the bioadhesive patch delivered and applied via the articulating linear stapler.

DETAILED DESCRIPTION

Figure 1A:
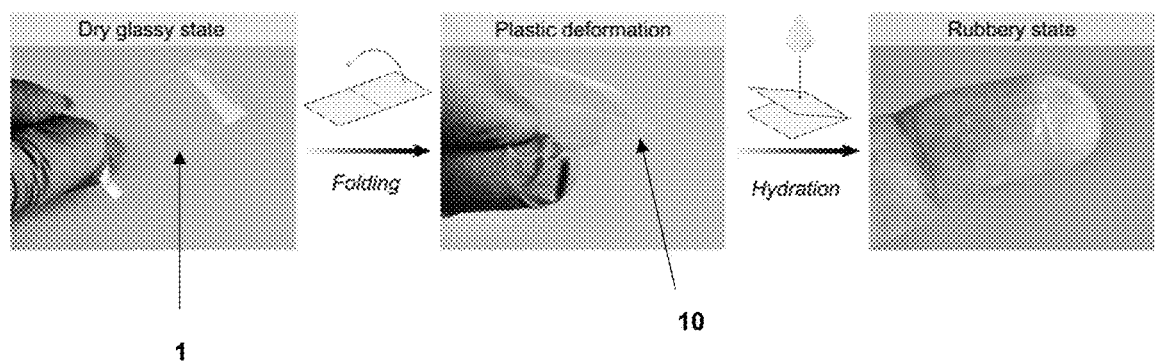
FIGS. 1A-C illustrate embodiments of the present invention bioadhesive material, where

The following definitions are useful for interpreting terms applied to features of the embodiments disclosed herein, and are meant only to define elements within the disclosure.

As used herein, the term "dry" when describing the bioadhesive layer of the present invention refers to a material that is below the equilibrium moisture content of the material in use. As such, when a dry bioadhesive layer of the present invention is placed in contact with a wet tissue or other wet or wetted (e.g., wetted by saline) surface to which it will adhere, the bioadhesive layer will absorb water, saline, moisture, and physiological body fluids such as blood plasma, interstitial fluid, lymphatic fluid, cerebrospinal fluid, and gastrointestinal fluid from the wet or wetted surface. Generally, a dry bioadhesive layer will have less than about 50% by weight of liquid components based on total weight of the dry adhesive material.

As used herein, the term "absorb" when describing the mechanism by which the dry bioadhesive layer absorbs water, saline, moisture, and physiological body fluids such as blood plasma, interstitial fluid, lymphatic fluid, cerebrospinal fluid, and gastrointestinal fluid from a wet surface in which it is placed in contact with, refers to atoms or molecules from the liquid of the wet surface crossing the surface of and entering the bioadhesive layer.

As used herein, the term "patch", "tape", "film", "strip", and "sheet", when describing the bioadhesive material of the present invention refers to a structure that has a relatively large area as compared to thickness. Such a structure provides flexibility.

As used herein, the terms "folded bioadhesive", "folded bioadhesive material", "folded bioadhesive patch", "folded bioadhesive tape", "folded bioadhesive film", "folded bioadhesive strip", and "folded bioadhesive sheet", and "folded bioadhesive sleeve" refers to the bioadhesive material of the present invention which has been specifically folded and/or cut (e.g., using origami- or kirigami-based techniques or other suitable techniques) and configured for integration with a particular minimally invasive surgical or diagnostic instrument. Thus, for example, a folded bioadhesive patch would be a bioadhesive patch that is initially in a generally flat configuration (where the "flat configuration" may include a microtexture on one or more surfaces) that has then been manipulated into a desired shape, e.g. by folding, and wherein that desired shape is maintained for integration on the minimally invasive device.

As used herein, the term "injectable bioadhesive" refers to bioadhesive materials that can generally be housed and deployed through instruments such as syringes and catheters. In particular, injectable bioadhesives refer to such materials that can be disposed within a conventional syringe having an outlet diameter of about 1 mm to 10 mm and can be pushed through and out of the syringe upon actuation of the plunger, and can also be passed through and out of a conventional minimally invasive cannula/catheter having an inner diameter of about 1 mm (3 Fr) to 11 mm (34 Fr). Such injectable bioadhesives will generally have a viscosity ranging between about 1 to 1,000 cSt.

As used herein, the term "microparticle" when used to describe the dry bioadhesive microparticles refers to a particulate form of the material with the average diameter no greater than about 200 µm, for example any value ranging from about 5 µm to about 200 µm. For example, the term microparticle may refer to a particulate form of the material with an average diameter of no greater than about 180 µm, no greater than about 160 µm, no greater than about 140 µm, no greater than about 120 µm, no greater than about 140 µm, no greater than about 120 µm, no greater than about 100 µm, no greater than about 80 µm, no greater than about 60 µm, no greater than about 40 µm, no greater than about 20 µm, and no greater than about 10 µm. However, any particle size ranging from about 5 µm to about 200 µm could be suitably selected depending upon the ultimate use of the adhesive material, and other factors such as desired rheological properties of the adhesive material. According to an exemplary embodiment, a suitable microparticle has size about 10 µm.

As used herein, the term "wet tissue" refers to biological tissues that contain or are covered (either entirely covered or partially covered to any extent) with aqueous media including water, saline, moisture, and physiological body fluids such as blood plasma, interstitial fluid, lymphatic fluid, cerebrospinal fluid, and gastrointestinal fluid.

As used herein, the term "instant" when used to describe the instant temporary crosslinks between the bioadhesive layer and one or more wet surfaces refers to a time elapse from the instant that the bioadhesive layer makes contact with the one or more wet surfaces of greater than zero seconds and up to or within about one minute, more preferably less than or equal to about 50 seconds, more preferably less than or equal to about 40 seconds, more preferably less than or equal to about 30 seconds, more preferably less than or equal to about 20 seconds, more preferably less than or equal to about 15 seconds, more preferably less than or equal to about 10 seconds, more preferably less than or equal to about 9 seconds, more preferably less than or equal to about 8 seconds, more preferably less than or equal to about 7 seconds, more preferably less than or equal to about 6 seconds, and more preferably less than or equal to about 5 seconds.

As used herein, the term "temporary" when used to describe the instant temporary crosslinks between the bioadhesive layer and one or more wet surfaces refers to a time range extending between time at which the instant temporary crosslinks form and the sufficiently long time such as over 24 hours after which the instant temporary crosslinks form.

As used herein, "fast" or "quick" when used to describe the fast covalent cross linking between the bioadhesive layer and one or more wet surfaces refers to a time elapse from the instant that the adhesive layer makes contact with the one or more wet surfaces of greater than zero seconds and up to and including 5 minutes, more preferably less than or equal to about 4.5 minutes, more preferably less than or equal to about 4 minutes, more preferably less than or equal to about 3.5 minutes, more preferably less than or equal to about 3 minutes, more preferably less than or equal to about 2.5 minutes, more preferably less than or equal to about 2 minutes, more preferably less than or equal to about 1.5 minutes, and more preferably less than or equal to about 1 minute.

As used herein, "swelling" when used to describe the bioadhesive layer absorption and swelling upon contact with one or more wet surfaces generally refers to an increase in size from that of the dry bioadhesive layer to that of the adhesive layer after absorption. The dry bioadhesive material is generally provided in the form of a patch, tape, sheet, or film, which is provided in a folded and/or cut (e.g., using origami- or kirigami-based techniques or other suitable techniques) configuration for integration with a particular minimally invasive surgical or diagnostic instrument, wherein the bioadhesive layer becomes thicker upon uptake of liquid, and which unfurls the folded configuration upon uptake of liquid.

As used herein, "biodegradable" when used to describe the adhesive material refers the decomposition and/or subsequent removal of the implanted adhesive material in part or whole within the living animals by the endogenous enzymes and/or water inside the animals.

As used herein, a "glassy state" when used to describe the bioadhesive material at room temperature refers to a state contingent on temperature and moisture content in which molecules within the bioadhesive material have reduced rotational and translational motion, resulting in a bioadhesive material exhibiting the physical properties of being relatively hard, brittle, and plastically deformable rather than viscous and rubbery.

The present invention generally provides bioadhesives and methods for deploying and adhering the bioadhesives using minimally invasive techniques. In particular embodiments, the present invention generally provides (i) bioadhesives and methods for sealing hollow structures (including, but not limited to airways, intestine, urogenital tract, heart) and blood vessels (including, but not limited to arterial and venous structures) by using an expanding balloon catheter to deploy a bioadhesive material disposed on the expanding balloon, and (ii) bioadhesives and methods for creating linear seals by using minimally invasive (e.g. thoracoscopic or laparoscopic) endoscopic instruments (including, but not limited to forceps, graspers, and endoscopic staplers) to deploy bioadhesives disposed on the endoscopic instruments externally onto tissues (including, but not limited to airways, intestine, urogenital tract, heart) and blood vessels (including, but not limited to arterial and venous structures).

According to embodiments of the present invention, a bioadhesive material is provided which is amenable to origami—(i.e., folding-based) and kirigami-based (i.e., cutting-based) manufacturing techniques, and is capable of holding a desired folded and/or cut structure until it is deployed for adhesion to a target tissue surface. The bioadhesive material is fabricated for adhesion to various body tissue surfaces. Generally, the bioadhesive material (i.e., unfolded bioadhesive material) has a configuration that is relatively thin in comparison to its length and width, thus enhancing the ability of the adhesive layer, once deployed, to conform to the tissue surface. As such, when adhered to a surface that moves, stretches, bends, twists, flexes, etc., the bioadhesive material will likewise move with the surface.

According to one aspect, the present invention provides a bioadhesive material comprising combination of: a hydrophobic matrix 22, particularly a hydrophobic oil matrix, and dry bioadhesive microparticles 20. According to an embodiment of the invention, the bioadhesive material is in the form of an injectable material comprising a hydrophobic matrix 22 with dry bioadhesive microparticles 20 dispersed therein (e.g., see FIG. 1C). The dry bioadhesive microparticles 20 are evenly dispersed within the hydrophobic matrix 22 such that the hydrophobic matrix 22 acts as a protective matrix (see FIG. 1C). Prior to use, one would preferably ensure that the bioadhesive material is a homogenous mixture of the dry bioadhesive microparticles 20 dispersed within the hydrophobic matrix 22 by vigorously shaking stirring, or the like. The preparation of such injectable bioadhesive materials is described in a copending U.S. patent application Ser. No. 17/110,841, which is incorporated by reference herein in its entirety.

In such injectable forms, the hydrophobic material can include, for example, oils such as silicone oils, mineral oils, essential oils, vegetable oils, and combinations thereof. Injectable bioadhesive materials of the present invention are designed to flow through a narrow structure, preferably structures used in minimally invasive procedures. For example, when disposed within a syringe, the bioadhesive material can be injected from the syringe and through minimally invasive instruments like catheters, for delivery to target tissue in a minimally invasive procedure (e.g., see FIG. 1C).

According to embodiments of the present invention, when the injectable bioadhesive is applied to a tissue surface covered in fluid (e.g., a blood-covered skin tissue) and gentle pressure is applied, the hydrophobic matrix 22 protects the dry bioadhesive microparticles 20 from the body fluids and repels the body fluids thereby clearing the surface. This allows the dry bioadhesive microparticles 20 to contact one another and contact the wet tissue surface. Subsequently, the dry bioadhesive microparticles 20 crosslink with each other and with the wet tissue surface to quickly form robust adhesion. As such, the present invention bioadhesive material provides fluid resistance to achieve instant robust adhesion of tissues covered by fluids (e.g., water, saline, moisture, interstitial fluids, and body fluids such as blood, saliva, gastrointestinal fluid, mucus, and succus).

In an exemplary embodiment, the injectable bioadhesive is delivered to a target tissue site through a syringe connected to a catheter. The catheter may be provided in the form of a balloon catheter, such that inflation of the balloon can be used to apply pressure to the bioadhesive material which triggers adhesion of the bioadhesive material to the target tissue.

According to one aspect, the dry bioadhesive microparticles 20 are formed from a dry bioadhesive material comprising a combination of: (i) one or more hydrophilic polymers or copolymers, (ii) one or more amine coupling groups, and (iii) one or more cross linkers as described herein.

According to a preferred embodiment, the dry bioadhesive microparticles 20 are prepared by first fabricating the bioadhesive material fabricated of a combination of (1) one or more hydrophilic polymers or copolymers, (ii) one or more amine coupling groups, and (iii) one or more cross-linkers, and deionized water. The as-prepared bioadhesive material is then dehydrated, and the dehydrated bioadhesive material is subjected to cryogenic grinding to produce dry bioadhesive microparticles 20 of a desired average particle size. For example, the dry bioadhesive may be first cut into small pieces, the dry bioadhesive pieces are then added to a stainless steel container with stainless steel balls, then the dry bioadhesive is ground under cryogenic condition by using a cryogenic ball mill to produce the dry bioadhesive microparticles 20. The thus formed dry bioadhesive microparticles 20 are then mixed with a desired hydrophobic matrix 22 at a desired ratio to prepare the injectable bioadhesive material, which may be injected through a syringe and catheter to a target site (e.g., a syringe with 2.5-mm diameter, a nozzle with 1.2-mm diameter).

According to embodiments of the present invention, the average size of the dry bioadhesive microparticles 20 can be controlled by the cryogenic grinding conditions (e.g., a grinding time fixed to 2 minutes and varying a grinding frequency from 10 Hz to 30 Hz (particularly 10 Hz, 15 Hz, 20 Hz, 25 Hz, and 30 Hz), wherein a higher grinding frequency resulted in a smaller average size of dry bioadhesive microparticles (~200 μm at 10 Hz and ~10 μm at 30 Hz). As such, a desired average size of the bioadhesive microparticles 20 can be achieved.

According to embodiments of the present invention, rheological properties (i.e., flow behavior, viscosity, shear yield stress) of the injectable bioadhesive are tunable by controlling one or more properties, particularly the mixing ratio between the dry bioadhesive microparticles 20 and the hydrophobic matrix 22. As such, by adjusting the ratio, the injectable bioadhesive material can range from viscous fluids to a stable thixotropic paste. According to exemplary embodiments, a mass ratio between the dry bioadhesive microparticles 20 and a hydrophobic matrix 22 can be selected from, for example, about 1:3, about 1:2, about 1:1, and about 1:0.5. According to an exemplary embodiment, a ratio between the bioadhesive microparticles and the hydrophobic matrix range from about 1:3 to about 1:0.5.

Reference will now be made in detail to embodiments of the present invention, examples of which are illustrated in the accompanying drawings. Wherever possible, the same reference numbers are used in the drawings and the description to refer to the same or like parts.

As depicted in FIG. 1, the present invention essentially comprises a bioadhesive patch 1 amenable to origami—(i.e., folding-based) and kirigami-based (i.e., cutting-based) manufacturing techniques, to provide a folded bioadhesive patch 10, thus allowing it to be integrated with and deployed by minimally invasive instruments actuated within the body. The bioadhesive material is a "dry" bioadhesive material that is in a glassy state at room temperature that maintains folded shapes due to plastic deformation, enabling it to be cut and folded into a variety of origami- and/or kirigami-based shapes adapted for disposal on a variety of minimally invasive surgical instruments. According to various embodiments, to allow for visualization of bioadhesive deployment and placement via ultrasound or radiography, the bioadhesive patch 1/folded bioadhesive patch 10 may contain one or more radiopaque markers (not shown) embedded therein and/or affixed to one or more surfaces thereof.

Figure 1B:
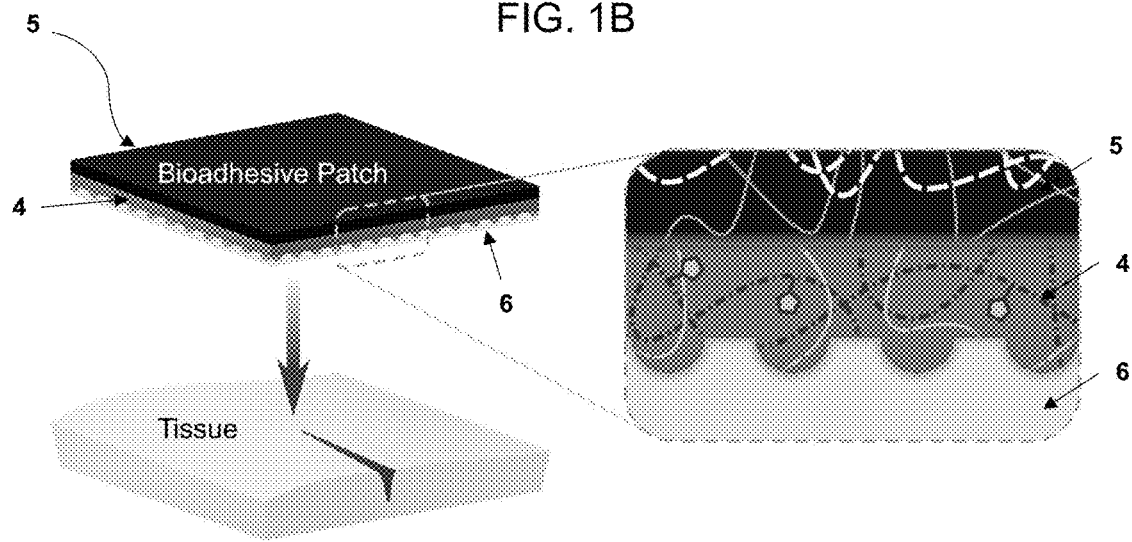
Figure 1C:
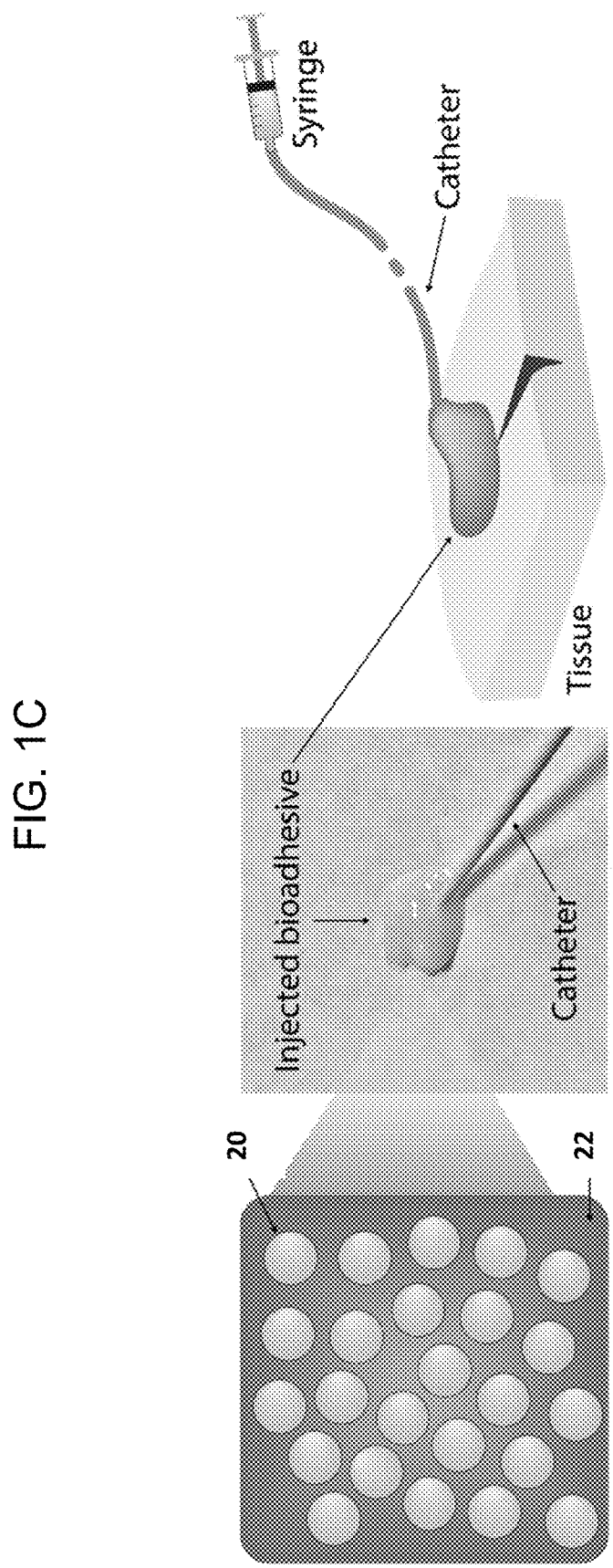

According to embodiments of the present invention, the folded bioadhesive patch 1 is fabricated and configured for achieving on-demand adhesion even in a wet environment, such as those encountered during minimally invasive procedures, which enables application to wet tissue surfaces. The bioadhesive patch 1 (in its unfolded or otherwise manipulated configuration) generally has a top surface 2 and a bottom surface 3, wherein the bottom surface 3 is specifically adapted for adhesion to a target tissue. In some embodiments, the bioadhesive patch 1 is configured with single-sided adhesiveness and, thus, the top surface 2 could be provided as a non-adhesive surface while the bottom surface 3 would be provided as an adhesive surface. If desired, dual-sided adhesiveness could also be provided by, for example, providing the top surface 2 with a removable non-adhesive surface layer (not shown) to expose an adhesive layer below or by providing the top surface 2 as an adhesive surface According to an embodiment, for example, as depicted in FIG. 1B, the bioadhesive patch 1 (shown in FIG. 1B in its unfolded configuration) has a multi-layer structure including an adhesive layer 4 with a non-adhesive layer 5 disposed thereon to provide the non-adhesive top surface 2. In these embodiments, the non-adhesive top surface 2 could form a surface that is in contact with the minimally invasive surgical instrument used in a given application. An opposing adhesive bottom surface 3 would then generally be disposed in an at least partially exposed state such that insertion of the minimally invasive surgical instrument into a target location and maneuvering the instrument to the target tissue surface would place the adhesive bottom surface of the bioadhesive patch 1 in contact with the target tissue surface. In some embodiments, the multi-layer structure contains only these two layers. In other embodiments, an overlayer 6 disposed on a side opposite the non-adhesive layer 5, thus sandwiching the adhesive layer 4 between the non-adhesive layer 5 and the overlayer 6. In an exemplary embodiment, the overlayer 6 is fabricated and configured to provide a hydrophobic interaction when placed in contact with the target surface, thereby repelling fluids (e.g., body fluids such as blood, mucus, saliva, gastric fluid, and/or interstitial fluid) and promoting adhesion between the adhesive layer 4 and the target surface.

The non-adhesive layer 5 can be fabricated of any material that provides a physical barrier preventing adhesion of the underlying surface of the adhesive layer 4 to tissues and surfaces in the environment in which the bioadhesive patch 1 is adhered. Such materials forming the non-adhesive layer are biocompatible when the adhesive patch is used on or near biological tissues. In some embodiments, the non-adhesive layer 5 is adapted to mitigate the risk of the formation of adhesions as the result of inflammation and coagulation. As such, the non-adhesive layer 5 may be fabricated of suitable anti-fouling materials including, but not limited to, collagen membranes, polymer or hydrogel films, and sprayable solutions. According to some embodiments, the non-adhesive layer 5 is formed of a zwitterionic hydrogel, or a biocompatible polymer or polymer blend (e.g., polyacrylic acid, polyacrylamide, polyvinyl alcohol, polyhydroxy ethyl methacrylate, polyethylene glycol, polyvinylpyrrolidone, polyurethane, polydimethylsiloxane or other silicone elastomers, polyvinyl chloride, styrene-ethylene-butylene-styrene (SEBS), gelatin, chitosan, alginate, polycaprolactone, polylactic acid, poly(lactic-co-glycolic acid)) functionalized with an interpenetrated network of zwitterionic polymers (e.g., poly(phospobetaine), poly(carboxybetaine), poly(sulfobetaine)).

According to embodiments of the present invention, the adhesive layer 4 is provided in the form of a dry adhesive material layer fabricated so as to provide a dry-crosslinking mechanism for instant strong adhesion to wet surfaces. Such adhesive compositions are described in copending U.S. patent application Ser. No. 16/846,293, which is incorporated by reference herein in its entirety. In particular, the adhesive layer 4 is formed of a combination of: (i) one or more hydrophilic polymers or copolymers that absorb water at the dry state (e.g., any conventional hydrophilic polymers or copolymers that absorb water at a dry state, including, but not limited to, polyacrylic acid (PAA), polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, alginic acid, pectin, and combinations thereof; particularly hydrophilic polymers or copolymers that contain one or more negatively-charged groups such as poly (acrylic acid), casein, albumin, and alginic acid, whose negatively-charged groups endow hygroscopic properties), (ii) one or more amine coupling groups (e.g., conventional amine coupling groups, including but not limited to, N-hydroxysuccinimide ester, N-hydroxysulfosuccinimide ester, aldehyde, imidoester, epoxide, isocyanate, catechol, and combinations thereof), and (iii) one or more cross linkers (e.g., conventional crosslinkers, including but not limited to gelatin methacrylate, hyaluronic acid methacrylate, oxidized methacrylic alginate, polycaprolactone diacrylate, N,N'-bis (acryloyl) cystamine, N,N'-methylenebis(acrylamide), polyethylene glycol diacrylate, polyethylene glycol dimethacrylate, and combinations thereof).

In an exemplary embodiment, the bioadhesive patch 1 is fabricated of an adhesive layer 4 comprised of poly(acrylic acid) grafted with N-hydroxysuccinimide ester (PAA-NHS ester) and chitosan, with a non-adhesive layer 5 of zwitterionic-interpenetrated polyurethane disposed on one surface of the adhesive layer 4.

According to embodiments of the present invention, the overlayer 6 is fabricated and configured to provide a hydrophobic interaction when placed in contact with the target surface, and can thus be formed of suitable hydrophobic fluids. Exemplary fluids include, but are not limited to oils, such as silicone oils, mineral oils, essential oils, vegetable oils, and combinations thereof.

As such, during application of such a multi-layer folded bioadhesive patch 1 according to the present invention, the overlayer 6 side of the folded bioadhesive patch 1 would be disposed so that at least a portion thereof is exposed and is placed in contact with the target tissue surface.

Figure 2:
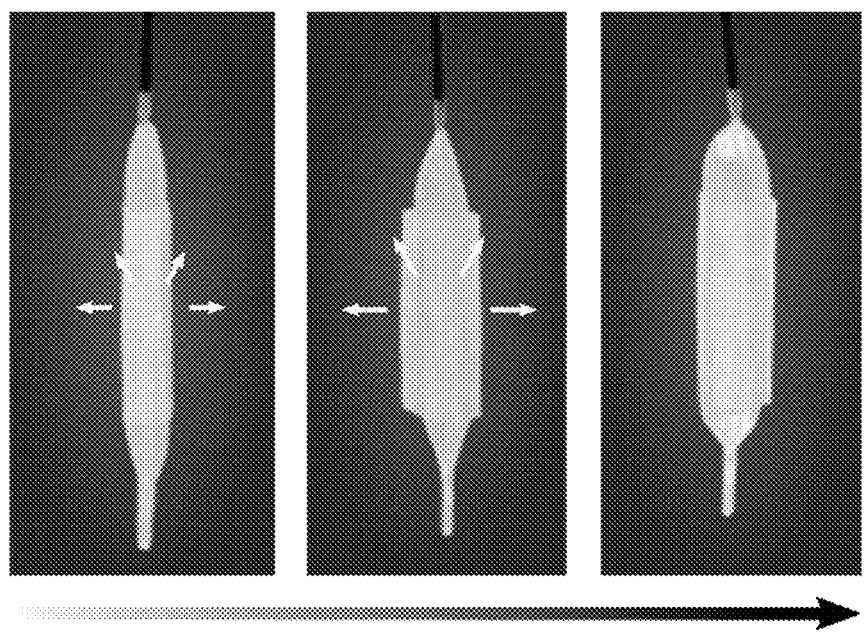
FIG. 2 shows photographs of a balloon catheter-based deployment mechanism for a bioadhesive material according to an embodiment of the present invention, wherein a folded bioadhesive patch provided in a target origami structure for disposal on the outer surface of an esophageal balloon catheter is depicted followed by an increase in inflation pressure of the balloon, which induces radial expansion and unfurling of the folded bioadhesive patch.
Figure 3A:
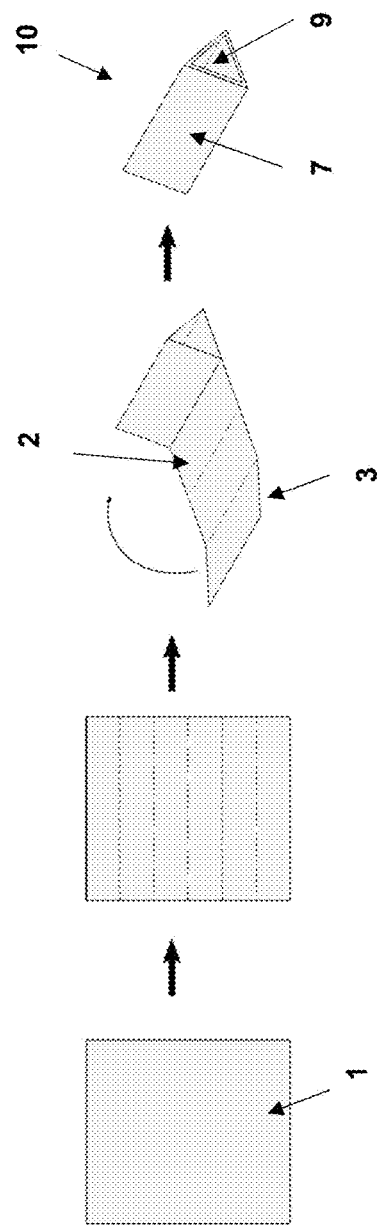
FIGS. 3A-B schematically illustrate folded bioadhesive designs for integration with and deployment by a balloon catheter, with FIG. 3A illustrating an origami-based design of a triangular sleeve bioadhesive and FIG. 3B illustrating an origami-based design of a pleated cylindrical sleeve with "wings", wherein the numbers of folds, edges, and wings may vary.
Figure 3B:
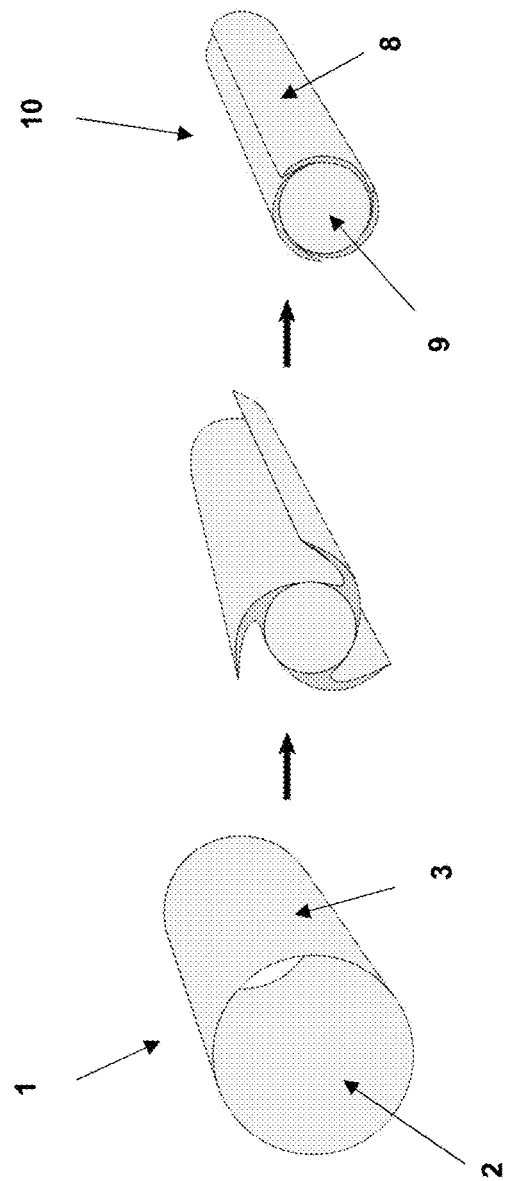

In one aspect of the invention, a method and system for achieving endoluminal sealing of tissue defects in tubular structures (e.g., the esophagus, the trachea, bronchi, vessels) is depicted in FIGS. 2-4. In particular, a conventional balloon catheter device would be used with a bioadhesive patch 1 folded into any variety of tubular sleeve structures to form the folded bioadhesive sleeve 10 (e.g., see FIGS. 3A-B) which would be disposed on the balloon catheter device circumscribing the uninflated balloon portion. In one embodiment, as illustrated in FIG. 3A, the bioadhesive patch 1 is folded into an origami-based design of a triangular folded bioadhesive sleeve 10, which may be sized and configured for disposal about the outer surface of an uninflated balloon of any variety of conventional balloon catheter devices. According to another embodiment, as illustrated in FIG. 3B, the bioadhesive patch 1 is folded into an origami-based design of a pleated cylindrical bioadhesive sleeve 10 with wings 7, wherein the design may be sized and configured for disposal about the outer surface of an uninflated balloon of any variety of conventional balloon catheter devices. The number edges 7 (portions between folds which form the exposed portions FIG. 3A) and wings 8 (portions between folds/pleats which form the exposed portions on the outside of the cylindrical sleeve, FIG. 3B) may vary. It is noted that while triangular and cylindrical folded bioadhesive sleeve 10 configurations are depicted, any other geometrical shapes (e.g., square, octagonal, etc.) are also encompassed by the present invention.

Regardless of the specific geometrical configuration, the bioadhesive patch 1 in the form of a folded bioadhesive sleeve 10 is provided with an inner passageway 9 in which the balloon is subsequently housed, the inner passageway 9 defined by folded portions of the non-adhesive side of the bioadhesive patch 1 (e.g., folded portions of the non-adhesive layer 5) and an outer adhesive surface defined by exposed folded portions (i.e., edges 7 or wings 8) of the adhesive side of the folded adhesive sleeve 10 (e.g. a surface of the adhesive layer 4 or, if present, the overlayer 6). In the embodiments depicted in FIGS. 3A-B, the folded origami-based designs are configured such that the folded bioadhesive sleeve 10 can be disposed on any conventional balloon catheter device, with the uninflated balloon portion housed within the inner passageway 9. In some embodiments, the folded bioadhesive sleeve 10 is mounted on the balloon catheter by simply sliding or placing the uninflated balloon within the inner passageway 9 by hand. In other embodiments, the folded bioadhesive sleeve 10 is mounted on the balloon catheter by first disposing the folded bioadhesive sleeve 10 inside of a cannula (not shown) through which the balloon catheter is inserted for a minimally invasive procedure. In this embodiment, the folded bioadhesive sleeve 10 would be housed within the tubular cannula such that the inner passageway 9 forms a passageway within the cannula through which the uninflated balloon portion of the device will be inserted, with an outer surface of the folded bioadhesive sleeve 10 disposed proximal to or in contact with an inner surface of the cannula. As such, when the uninflated balloon portion of the device is inserted into the cannula, the uninflated balloon slides into the folded bioadhesive sleeve 10 inner passageway 9, with the outer surface of the uninflated balloon in contact with the inner non-adhesive side of the folded bioadhesive sleeve 10. The folded bioadhesive sleeve 10 can be held in place about the uninflated balloon by frictional force and suitable design of the folded bioadhesive sleeve 10 dimensions based on the balloon catheter dimensions being used in a given case. For example, currently available balloon catheters incorporate balloons which, when uninflated, provide diameters ranging from about of 2 mm to about 6 mm (6 French-18 French). As such, a variety of folded bioadhesive sleeves 10 can be designed, each with various inner passageway 9 diameters for suitably fitting over these standard balloon catheter designs. Further, during use, when the balloon is inflated and the folded bioadhesive sleeve 10 comes into contact with a target tissue surface and body fluids (or injected saline or other fluids), the folded bioadhesive sleeve 10 unfolds (as described in greater detail herein). As such, the folded bioadhesive sleeve 10 is further configured such that upon expansion of the balloon, it unfolds to accommodate the inflating balloon to prevent tearing of the bioadhesive. The inflated diameter of the balloon would depend on the anatomy of the particular patient and the location in which the balloon catheter is being used. Generally, the following ranges of inflated balloon diameters would be suitable in designing the unfolding configuration of the folded balloon sleeve 10: about 10-25 mm for tracheal delivery, about 10-20 mm for esophageal delivery, and about 20-35 mm for ascending aorta delivery. Thus, the folded balloon sleeve 10 will have an unfolding configuration that accommodates at least these inflated balloon diameters, preferably the larger diameter of the range to avoid potential tearing of the bioadhesive.

According to some embodiments, the folded bioadhesive sleeve 10 may further include one or more stabilizing elements (not shown, e.g., adhesive, tab or string-like element, stiffening member, or other suitable stabilizing mechanisms) that are attached to or integrated with the balloon catheter upon disposal of the folded bioadhesive sleeve 10 on the uninflated balloon. Such stabilizing elements are configured to restrict the movement, bunching, or rotation of the folded bioadhesive sleeve 10 during maneuvering and positioning of the balloon catheter to a target site. For example, a stiffening member may be attached to the balloon catheter and folded bioadhesive sleeve 10 to hold the folded bioadhesive sleeve 10 in place on the balloon portion, where the stiffening member undergoes detachment from the folded bioadhesive sleeve 10 upon deployment (e.g., by dissolving, breaking, or moving during balloon inflation).

According to the present invention as depicted in FIGS. 2 and 4A-D, a folded bioadhesive sleeve 10 is fabricated and configured such that, as the balloon inflates, the bioadhesive sleeve 10 unfurls (e.g., the pleated wings may unfurl or, in the case of the triangular sleeve the folded structure would unwrap and expand (e.g., see FIGS. 4A-D; FIGS. 3A-3B sequence in reverse). As the balloon inflates and the folded bioadhesive sleeve 10 unfurls, the outer adhesive side of the bioadhesive meets the walls of the hollow organs or vessel in which it is inserted. As the inflation pressure of the balloon continues to increase, the radial pressure exerted by the balloon on the bioadhesive and tissue walls of the hollow organ or vessel, which triggers adhesion of the bioadhesive material, resulting in rapid and robust endoluminal sealing. Upon hydration (in the presence of body fluids and wet tissue surfaces) and adhesion of the bioadhesive material on the wet tissue surfaces, the bioadhesive material transits into a rubbery state (FIG. 1), releasing the plastic deformation of its folded state and conforming to the tissue surface.

According to an exemplary embodiment, ex vivo demonstrations using minimally invasive delivery devices and techniques to seal a porcine trachea, esophagus, and aorta, respectively using the present invention folded bioadhesive sleeve 10 are illustrated in FIGS. 4B-D. It is noted that the demonstrations are also applicable to a variety of additional organs and surgical sites. In particular, in FIGS. 4B-D, different balloon catheters adapted for the diameters of the different target organs and vessels were used to demonstrate the ability of the present materials and methods to endoluminally deliver and adhere a bioadhesive in the configuration of a folded bioadhesive sleeve 10 to the target organs and vessels. In particular, it was demonstrated that a Foley catheter can be used with the present invention folded bioadhesive sleeve 10 to achieve air-tight sealing of a lacerated porcine trachea with a 5-mm circular transmural defect, allowing for normal inflation of the lung after sealing (FIG. 4B). Similarly, rapid fluid-tight and hemostatic endoluminal sealing of 5-mm circular transmural defects in a porcine esophagus (FIG. 4C) and aorta (FIG. 4D) was achieved through balloon catheter-based folded bioadhesive sleeve 10 deployment. These seals achieved by the endoluminally-delivered folded bioadhesive sleeves 10 were demonstrated to readily withstand supraphysiological pressures of over 300 mmHg.

According to embodiments of the present invention, the size and shape of the folded bioadhesive sleeves 10 adapted for balloon catheter-based delivery can further be customized according to specific clinical indications, thus providing focal defect coverage in addition to the circumferential sealing exemplified in these demonstrations.

According to another embodiment, the present invention bioadhesive materials and methods of application are configured for creating linear tissue seals in tissue using an articulating linear stapler adapted for minimally invasive procedures. In particular, a folded bioadhesive sleeve 10 is configured for wrapping about or enclosing an articulating head portion of a linear stapler (i.e., the portion extending from the elongate tubular portion, which includes two opposing jaws and a hinge-like connector between the opposing jaws). In this embodiment, one or more portions of the folded bioadhesive sleeve 10 includes one or more adhesive portions 17 disposed thereon for placement and adhesion by actuation of the jaws.

Figure 5:
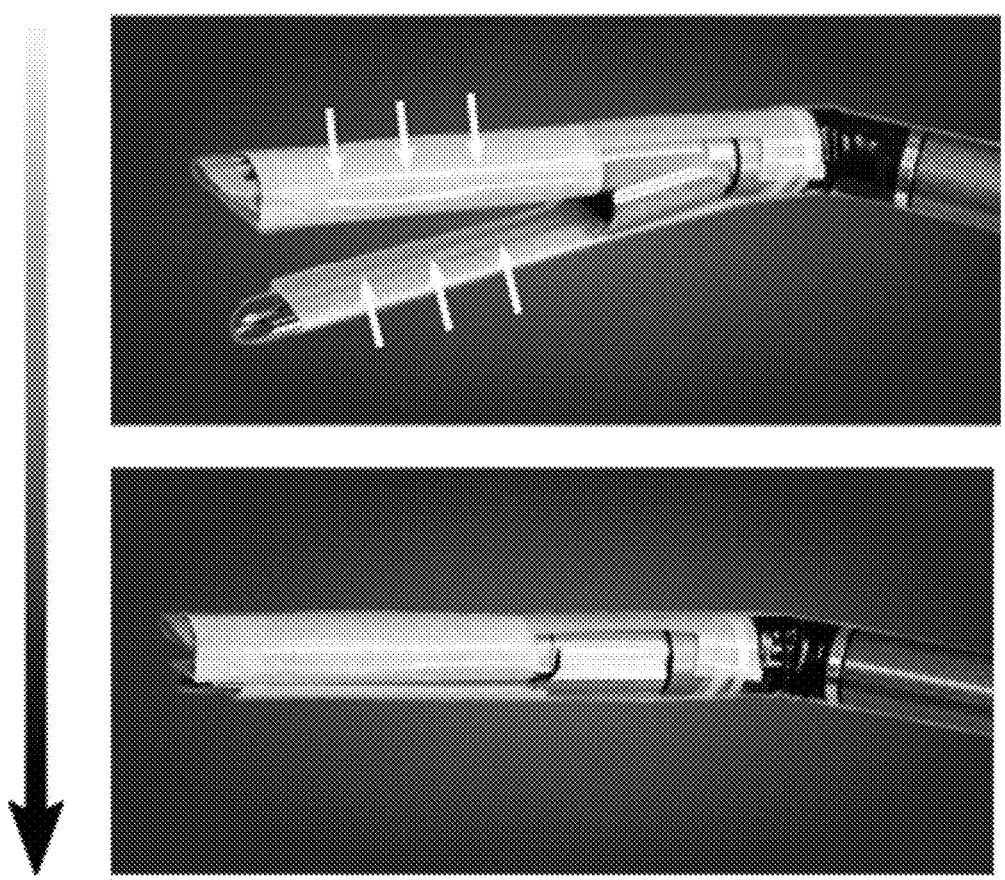
FIG. 5 schematically illustrates a stapler catheter-based bioadhesive patch deployment mechanism according to an embodiment of the present invention, wherein an articulating linear stapler configuration is depicted and wherein clamping of the stapler jaws applies compression pressure to one or more adhesive patches disposed in a folded sleeve configuration on one or more of the stapler jaws.
Figure 6:
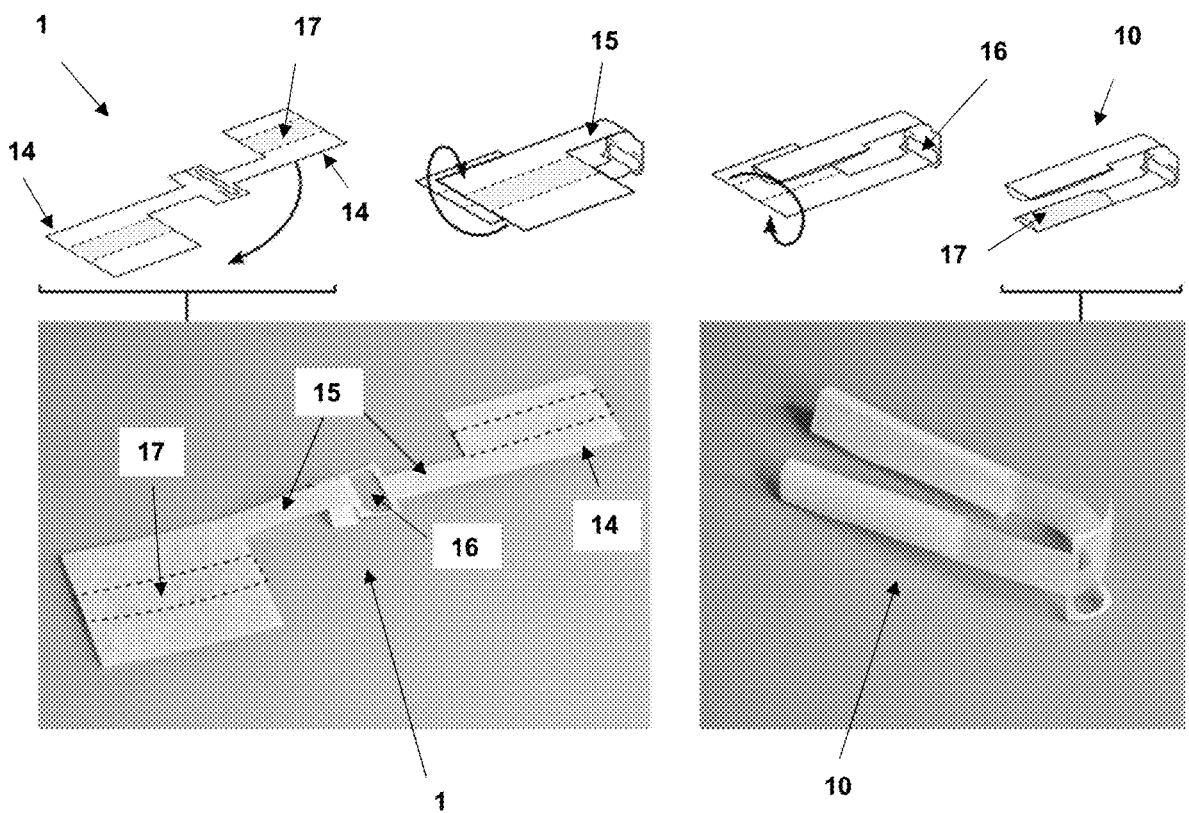
FIG. 6 schematically illustrates an origami-based design for integration with a surgical stapler according to an embodiment of the preset invention, wherein a folded sleeve design configured to fit over the anvil and stapler cartridge of a surgical stapler includes rectangular bioadhesive layers (indicated by dashed lines) suitably positioned for deployment by stapler actuation.

According to a preferred embodiment, as depicted in FIG. 6, a pre-folded bioadhesive sleeve 1 is provided in the shape of two rectangular portions 14 each sized and shaped for wrapping about (preferably surrounding) opposing articulating jaws of the stapler, the two rectangular portions 14 interconnected by two extensions 15 sized and shaped to extend along a distal portion of the articulating head, the two extensions 15 meeting at a central opening 16 adapted to fit the hinge-like connector and elongate tubular portion of the stapler therethrough. As shown in FIG. 6, two adhesive portions 17 may be disposed on each opposing rectangular portion 14 such that, when the folded adhesive sleeve 10 is integrated with the articulating linear stapler, each adhesive portion 17 is positioned on opposing inner jaw surfaces, with the adhesive portions 17 being exposed for contact with a target tissue surface (e.g., see FIG. 5).

During use, the articulating linear stapler, with the jaws in an open position, is maneuvered to the target tissue site (i.e., defect in the tissue) using minimally invasive procedures. Upon reaching the target tissue, the stapler jaws are disposed about the target tissue site (i.e., with the target tissue/defect disposed between the stapler jaws), such that actuation of the stapler jaws (i.e. squeezing the jaws together) causes the adhesive portions 17 of the folded bioadhesive sleeve 10 to contact the target tissue surface, and further compresses the adhesive portions 17 against the target tissue surface. This contact and compression of the adhesive portions 17 against the target tissue surface triggers adhesion and subsequent sealing of the defect.

According to embodiments of the present invention, in addition to deploying an adhesive using the articulating linear stapler, the articulating linear stapler may house a stapler cartridge and, thus, actuation of the jaws may also include the firing of the staple cartridge. In this case, actuation of the stapler jaws would provide staple lines buttressed with the bioadhesive Alternatively, these steps may be performed without the insertion of staples, resulting in a staple-free linear seal.

In an exemplary embodiment, a PAA-NHS and chitosan-based dry bioadhesive layer 4 is backed with a non-adhesive layer 5 of zwitterionic-interpenetrated polyurethane to form a multi-layer bioadhesive. This multi-layer bioadhesive is cut into rectangular strips to form adhesive portions 17 fit to the dimensions of the jaws of an endoscopic articulating linear stapler. While rectangular strips are preferred, other geometric shapes such as square, oval, circular, etc. may alternatively be used. The non-adhesive layer 5 of the adhesive portion 17 is positioned on the folded bioadhesive sleeve 10 which is designed to fit over the jaws of the stapler (FIG. 6), thus holding the adhesive portions 17 precisely in place as the articulating stapler is inserted and maneuvered to a target tissue site using minimally invasive techniques. When the stapler reaches the target tissue site and positioned suitably relative to the target tissue site/defect, the stapler is actuated causing the adhesive portions 17 to compress onto/around the target tissue site/defect. Upon compression against the tissue surface, and adhesion to the tissue surface, the adhesive portions 17 are released from the folded bioadhesive sleeve 10, creating an air and fluid-tight seal on the target tissue. In particular, adhesion formation between the adhesive portions 17 and the tissue surface is relatively much stronger than adhesion between the adhesive portions 17 and the folded bioadhesive sleeve 10. As a result, the adhesive portions 17 preferentially adhere to the tissue and peel away from folded bioadhesive sleeve 10. In some embodiments, an additional securing mechanism (not shown) is provided for securing the adhesive portions 17 to the folded bioadhesive sleeve 10. During implantation, this additional securing mechanism is removed (e.g., in the case of a water-soluble adhesive which is used as an additional securing mechanism to bond the adhesive portions 17 to the folded bioadhesive sleeve 10, dissolving of this adhesive upon hydration results in release of the adhesive portions 17 from the folded bioadhesive sleeve 10).

In the case of rectangular adhesive portions 17, a linear seal is formed on the target tissue. According to an embodiment of the invention, as depicted in FIG. 6, opposing rectangular adhesive portions 17 are disposed on each opposing jaw and, as such, a linear seal is formed on both sides of target tissue. Should there be only a need for one-sided adhesion (e.g., when covering a small perforation on a single side of a tissue), the deployment strategy can be adjusted accordingly and a single adhesive portion 17 could be disposed on one jaw of the articulating stapler and deployed to the affected site.

Figures 7A, 7B, 7C:
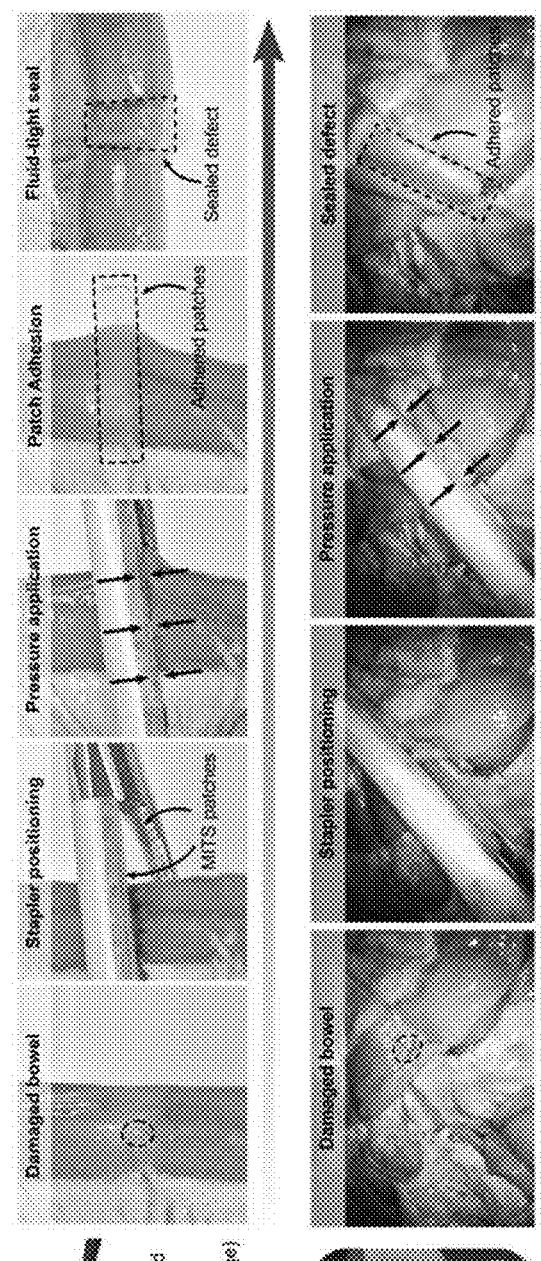

Using the articulating stapler and opposing adhesive portions 17 disposed on each of the articulating stapler jaws via a folded bioadhesive sleeve 10, fluid-tight sealing of an exemplary 5-mm circular transmural defect in a segment of an ex vivo porcine intestine was demonstrated as illustrated in FIGS. 7A-B. In order to further simulate the method in a minimally invasive surgical setting, the sealing of another porcine intestine with a 5-mm circular transmural defect was performed with endoscopic visualization to guide the delivery and application processes of an articulating stapler with opposing adhesive portions 17 disposed on each of the articulating stapler jaws via a the folded bioadhesive sleeve 10 (FIG. 7C). As demonstrated, fluid-tight sealing of the 5-mm circular transmural defect was achieved.

The bioadhesive materials, devices, and methods of the present invention will be further illustrated with reference to the following examples which are intended to aid in the understanding of the embodiments of the present invention, but which are not to be construed as a limitation thereof.

Materials and Methods

In the various examples, the following materials and methods were used unless otherwise noted.

Preparation of the Bioadhesive Patch

To prepare the bioadhesive precursor solution, 30 w/w % acrylic acid, 2 w/w % chitosan (HMC+ Chitoscience Chitosan 95/500, 95% deacetylation), 1 w/w % acrylic acid N-hy droxysuccinimide ester, 0.2 w/w % α-ketoglutaric acid, and 0.05 w/w % Poly(ethylene glycol methacrylate) (PEGDMA; Mn=550) were dissolved in deionized water. The precursor solution was poured on a glass mold with spacers (the thickness is 210 μm unless otherwise mentioned) and cured in a UV chamber (284 nm, 10 W power) for 30 min. To create a micro-textured surface, microparticles of the dry bioadhesive layer were prepared by cryogenic grinding (CryoMill, Retsch) at 30 Hz frequency for 2 min and then applied on an as-prepared bioadhesive layer by using a sieve with 100-μm pore size. To create a bioadhesive paste, the dry bioadhesive layer as formed is broken down to provide bioadhesive microparticles, which were then suspended in a hydrophobic fluid as described herein.

To prepare the zwitterionic backing layer, 10 w/w % hydrophilic PU (HydroMed™ D3, Advansource Biomaterials) and 0.1 w/w % benzophenone dissolved in ethanol/water mixture (95:5 v/v) was spin-coated at 200 rpm. The spin-coated film was dried under airflow overnight, then submerged into an aqueous solution containing 35 w/w % [2-(Methacryloyloxy)ethyl]dimethyl-(3-sulfopropyl)ammonium hydroxide (DMAPS) and 5 w/w % α-ketoglutaric acid for 10 min, followed by curing in a UV chamber (284 nm, 10 W power) for 1 hour. The resultant film was thoroughly washed in a large volume of deionized water for 3 days to remove unreacted reagents, then thoroughly dried under airflow.

To combine the zwitterionic backing layer with the bioadhesive layer, a thin layer of 5 w/w % hydrophilic PU solution in ethanol/water mixture (95:5 v/v) was spin-coated at 400 rpm over the flat surface of the bioadhesive layer. The zwitterionic backing layer was then introduced and the entire assembly was thoroughly dried. To introduce the hydrophobic-liquid overlayer, silicone oil (100 cSt viscosity) was impinged on the micro-textured surface of the bioadhesive layer.

Ex vivo Demonstrations

All ex vivo experiments were reviewed and approved by the Committee on Animal Care at the Massachusetts Institute of Technology.

For sealing of a tracheal defect, a 5-mm diameter hole was punched into the wall of a porcine trachea using a biopsy punch. The upper portion of the trachea was connected to a tubing, through which air was pumped to inflate the lung lobes. A bioadhesive patch was folded via the origami-based design and fabrication process described herein and introduced to a Foley catheter (ReliaMed). The Foley catheter carrying the folded bioadhesive patch was inserted via the proximal lumen of the damaged trachea. Once the patch delivery system was appropriately positioned in relation to the tracheal defect, the balloon was inflated to apply pressure to the folded bioadhesive patch and the walls of the trachea for 5 sec to seal the defect. After the sealing of tracheal defect, air was pumped through the trachea to check the air-tight sealing of the trachea and restored inflation capability of the lung lobes.

For sealing of an esophageal defect, a 5-mm diameter hole was generated in the wall of a porcine esophagus using a biopsy punch. Water was infused through the esophagus, generating a pressure of 100 mm Hg using a tubing and a peristaltic pump (Thermo Fischer) to visualize leakage through the defect. A bioadhesive patch was folded via the origami-based design and fabrication process described herein and introduced to an esophageal catheter (Boston Scientific). The esophageal catheter carrying the folded bioadhesive patch was inserted into the proximal lumen of the damaged esophagus. Once the catheter was maneuvered to the desired deployment position at the site of the defect, the balloon was inflated to apply a pressure around 77.5 kPa to the folded bioadhesive patch and the walls of the esophagus for 5 sec to seal the defect. After sealing the esophageal defect, water was pumped through the esophagus to confirm the fluid-tight sealing.

For sealing of an aortic defect, a 5-mm diameter hole was punched in the wall of a porcine aorta using a biopsy punch. Porcine blood was perfused through the aorta, generating a pressure of 120 mm Hg using a tubing and a peristaltic pump (Thermo Fischer) to visualize leakage through the defect. A bioadhesive patch was folded via the origami-based design and fabrication process described herein and introduced to a Foley catheter (ReliaMed). The Foley catheter with the folded bioadhesive patch was inserted into the lumen of the damaged aorta. Once the catheter was maneuvered to the desired deployment position at the site of the defect, the balloon was inflated to apply pressure to the folded bioadhesive patch and the walls of the aorta for 5 sec to seal the defect. After the sealing of aortic defect, porcine blood was pumped through the aorta to confirm the fluid-tight sealing of the aorta.

For sealing of an intestinal defect, a 5-mm hole was created in a porcine small intestine wall using a biopsy punch. A dual-sleeve (i.e., folded bioadhesive sleeve) with two opposing adhesive portions was prepared according to the origami- and kirigami-based design and fabrication process described herein and introduced to an articulating linear stapler (Ethicon) on opposing jaws of the stapler. The articulating linear stapler with the folded bioadhesive sleeve disposed thereon was navigated to the defect site and actuated to apply compression for 5 sec. The repaired intestine was connected to a pump and inflated with water to confirm fluid-tight sealing of the bowel under a pressure of 120 mm Hg.

To simulate a minimally invasive surgical setting, the described experiments were repeated using a dark chamber with access ports for the endoscopic device, and a waterproof endoscope camera (DEPSTECH) was used for visualization.

What is claimed is:

1. A folded bioadhesive sleeve for introduction to a target tissue surface using minimally invasive techniques comprising:
    a multilayer bioadhesive material comprising a dry bioadhesive layer having a bottom surface and a top surface, and a non-adhesive layer disposed on the top surface of the dry bioadhesive layer;
    wherein the multilayer bioadhesive material is in the configuration of a multilayer bioadhesive patch, tape, film, strip, or sheet,
    wherein the multilayer bioadhesive materials is folded into a hollow sleeve shape comprising an inner passageway and an outer surface, wherein the inner passageway is defined by an inner surface formed of portions of the non-adhesive layer,
    wherein the outer surface is an adhesive surface;
    wherein, in a folded configuration, the multilayer bioadhesive material is configured to be in an origami-based design; and
    wherein the bottom surface of the dry bioadhesive layer is micro-textured,
    wherein the micro-textured surface is configured to comprise a plurality of surface imbedded microparticles, embossed micropatterns, molded micro-textures, patterned micro-textures, surface etched textures, spun micro- or nano-fibers, or combinations thereof.

2. The folded bioadhesive sleeve of claim 1, wherein the dry bioadhesive layer has a liquid content such that placement of a surface of the dry bioadhesive layer in contact with the target tissue surface causes the dry bioadhesive layer to absorb liquid present on the target tissue surface, swell to form temporary crosslinking between the dry bioadhesive layer and the target tissue surface, and form covalent crosslinking between the dry bioadhesive layer and the target tissue surface.

3. The folded bioadhesive sleeve of claim 2, wherein the dry bioadhesive layer comprises (i) one or more hydrophilic polymers; (ii) one or more amine coupling groups, and (iii) one or more cross linkers.

4. The folded bioadhesive sleeve of claim 1, further comprising a hydrophobic overlayer disposed on the bottom surface of the dry bioadhesive layer.

5. The folded bioadhesive sleeve of claim 4, wherein the hydrophobic overlayer comprises one or more oils.

6. The folded bioadhesive sleeve of claim 1, wherein the non-adhesive layer comprises a biocompatible polymer or polymer blend.

7. The folded bioadhesive sleeve of claim 1, wherein the origami-based design is of a triangular sleeve having a triangular shaped inner passageway.

8. The folded bioadhesive sleeve of claim 1, wherein the triangular sleeve is sized and shaped for housing a distal portion of a minimally invasive device.

9. The folded bioadhesive sleeve of claim 8, wherein the minimally invasive device is a balloon catheter, and the triangular sleeve is sized and shaped for housing an uninflated balloon.

10. The folded bioadhesive sleeve of claim 1, wherein the origami-based design is of a pleated cylindrical sleeve with a plurality of wings.

11. The folded bioadhesive sleeve of claim 1, wherein the pleated cylindrical sleeve is sized and shaped for housing a distal portion of a minimally invasive device.

12. The folded bioadhesive sleeve of claim 11, wherein the minimally invasive device is a balloon catheter, and the pleated cylindrical sleeve is sized and shaped for housing an uninflated balloon.

13. The folded bioadhesive sleeve of claim 1, further comprising one or more stabilizing elements disposed on the bioadhesive, including an adhesive, a tab or a string-like element, a stiffening member, or other suitable stabilizing mechanisms configured to restrict the movement, bunching, or rotation of the folded bioadhesive sleeve, during attachment to a minimally invasive device.

14. A method of adhering a bioadhesive to a tissue surface using a minimally invasive techniques, wherein the tissue surface is an inner surface of a hollow organ or vessel, comprising:

providing the folded bioadhesive sleeve of claim 1;
providing a balloon catheter device having an uninflated balloon on a distal end thereof;
disposing the folded bioadhesive sleeve over the uninflated balloon, with the inner passageway at least partially housing the uninflated balloon, and wherein the inner surface of the folded bioadhesive sleeve is in contact with the uninflated balloon;
inserting the balloon catheter device into the hollow organ or vessel at a target tissue surface site using the minimally invasive techniques;
inflating the balloon and allowing the folded bioadhesive sleeve to unfurl such that the outer adhesive surface contacts the inner surface of the hollow organ or vessel; and
allowing a combination of hydration of the dry bioadhesive layer in the presence of body fluids and radial pressure exerted by the inflated balloon to release the folded configuration, conform the bioadhesive material to the inner surface of the hollow organ or vessel, and trigger adhesion of the bioadhesive material to the inner surface of the hollow organ or vessel.

* * * * *